United States Patent [19]
Chatterjee

[11] 3,932,209
[45] Jan. 13, 1976

[54] LOW HEMICELLULOSE, DRY CROSSLINKED CELLULOSIC ABSORBENT MATERIALS

[75] Inventor: Pronoy Kumar Chatterjee, Spotswood, N.J.

[73] Assignee: Personal Products Company, Milltown, N.J.

[22] Filed: Aug. 9, 1971

[21] Appl. No.: 169,957

Related U.S. Application Data

[62] Division of Ser. No. 803,525, Feb. 24, 1969, abandoned.

[52] U.S. Cl.............. 162/157 C; 8/116.2; 162/146
[51] Int. Cl.².......................................... D21H 5/14
[58] Field of Search.......... 162/146, 157 C; 8/116.2, 8/116.4, 116 R

[56] References Cited
UNITED STATES PATENTS

| | | | |
|---|---|---|---|
| 2,940,817 | 6/1960 | Browne | 8/116.2 |
| 2,971,815 | 2/1961 | Bullock et al. | 8/116.2 |
| 3,069,311 | 12/1962 | Harpham et al. | 162/157 C |
| 3,224,926 | 12/1965 | Bernardin | 162/146 |
| 3,339,550 | 9/1967 | Van Haaften | 128/290 R |
| 3,395,708 | 8/1968 | Hervey et al. | 162/179 X |
| 3,440,135 | 4/1969 | Chung | 162/157 C |
| 3,485,575 | 12/1969 | Christian et al. | 8/116.2 |
| 3,535,202 | 10/1970 | Huang | 162/166 |

FOREIGN PATENTS OR APPLICATIONS 1,095,505   12/1967   United Kingdom

*Primary Examiner*—Robert L. Lindsay, Jr.
*Assistant Examiner*—William F. Smith
*Attorney, Agent, or Firm*—Jason Lipow

[57] ABSTRACT

Dry crosslinked, fibrous cellulosic absorbent material having low hemicellulose content and low knot content, the fibers being internally crosslinked for the major part and being relatively free of intercrosslinking with adjacent fibers.

3 Claims, 9 Drawing Figures

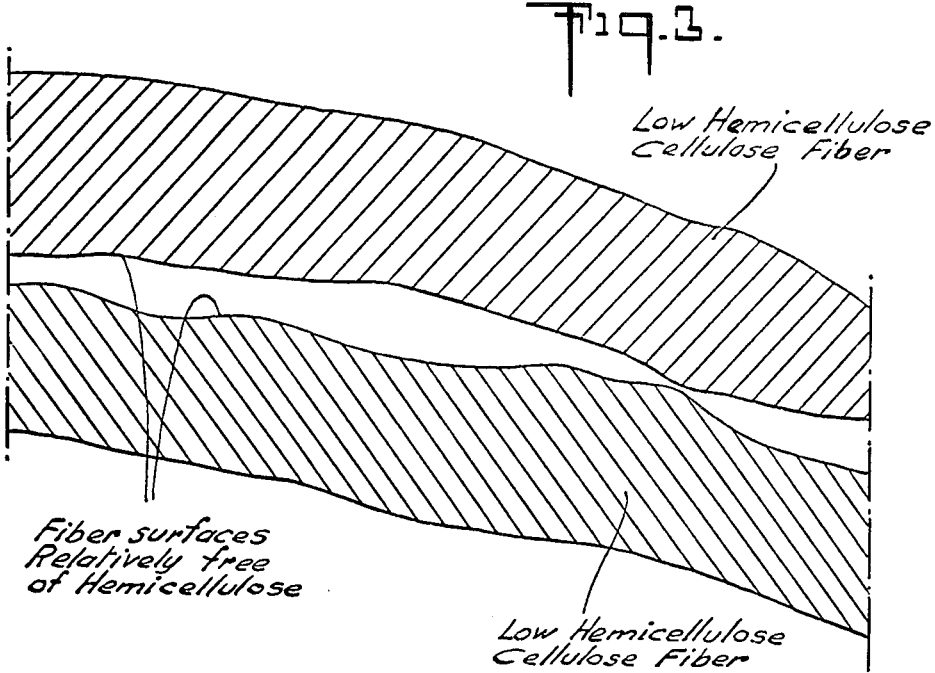
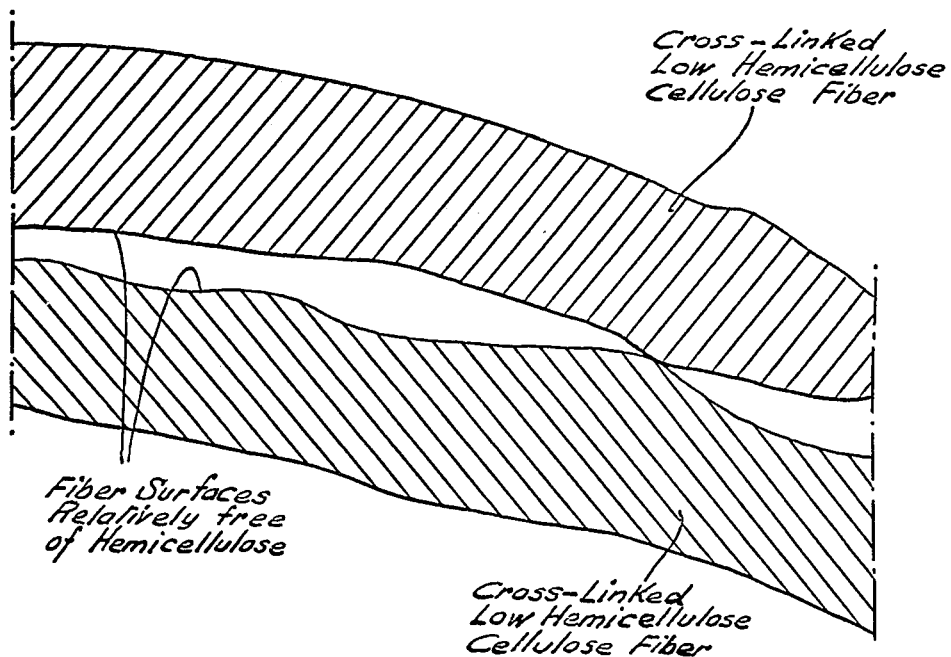

LOW HEMICELLULOSE, DRY CROSSLINKED CELLULOSIC ABSORBENT MATERIALS

This is a divisional application of U.S. patent application Ser. No. 803,525, filed Feb. 24, 1969, now abandoned.

The present invention relates to absorbent products for absorbing fluids, and more particularly, is concerned with fibrous cellulosic products having increased fluid absorption and retention capacities, improved dry and wet resilience, and low knot content.

Absorbent products for absorbing and retaining body exudates and fluids such as sanitary napkins, diapers, hospital underpads, filter pads, surgical dressings, tampons, and the like, usually contain fibrous absorbent materials of a cellulosic origin, usually wood pulp fluff. Other fibrous absorbent materials are often used but wood pulp fluff is normally preferred, particularly for economic reasons.

The wood pulp fluff is usually prepared by grinding pulpboard in a hammer mill or in other commercial shredding or grinding devices and is delivered in fluffed form to a production line where it is incorporated in the particular product being manufactured. Such wood pulp fluff normally has excellent fluid absorption and retention properties and acceptable dry and wet resilience. Its low cost and other economic advantages, of course, do not neet repeating.

Wood pulp fluff has been used for many years with satisfactory results but it is always desirable to improve existing products and materials, no matter how satisfactory or acceptable they have been in the past.

For example, in recent years, there have been several efforts made in the direction of crosslinking cellulosic fibrous materials such as wood pulp fluff in order to improve their fluid-absorbency and fluid-retention properties, along with their dry and wet resilience.

Crosslinking cellulosic fibers may be obtained by reacting cellulosic fibers with a material one or more molecules of which are capable of combining with at least two hydroxyl groups in the cellulose molecule, or in adjacent cellulose molecules. The reactive groups of the crosslinking agent which combine with the hydroxyl groups may exist prior to the reaction with cellulose, as in the case of glyoxal, or they may be generated during the reaction with the cellulose, as in the case of the sodium thiosulfate derivative of divinyl sulfone. In order to crosslink cellulose, the crosslinking agent must be at least difunctional with respect to cellulose, e.g., it must react with at least two hydroxyl groups. Formaldehyde, for example, is monofunctional with regard to many substances; it is, however, difunctional with respect to cellulose. In many polyfunctional materials of the type that react with two or more hydroxyl groups, one reactive group of the polyfunctional material may react more rapidly than other groups. Consequently, within a given reaction time, not all of the reactive groups on a molecule of the polyfunctional material may react with the hydroxyl groups in the cellulose molecule to form crosslinks; only one of the reactive groups may so react. Crosslinking occurs when at least two of the reactive groups in a molecule of the polyfunctional material react.

Cellulose can be crosslinked in a number of ways and, in accordance with current concepts, may be dry crosslinked or wet crosslinked. The two types of crosslinking refer to the manner in which the crosslinking is done.

Dry crosslinked cellulose is obtained when the cellulose is in a collapsed state at the time of crosslinking. A collapsed state is obtained by removing most or all of the water which causes the fiber to swell. In one known procedure, the cellulose is passed through a boric acid solution, dried, and then heated in a sealed tube in the presence of paraformaldehyde. The fibers are then washed free of unreacted material. A more common technique is to apply the crosslinking agent and a catalyst to the cellulose in an aqueous bath, drive off the water in a drying step, and react the crosslinking agent with the cellulose in a subsequent curing step.

Wet crosslinked cellulose is obtained when the crosslinking agent is reacted with the cellulose while the cellulose is in a swollen state. Ordinarily, the cellulose is maintained in a swollen state by water which is present during the reaction. However, techniques have been developed whereby the cellulose can be maintained in a swollen state in the absence of water by using in lieu thereof an inert, non-volatile substance. Cellulose fibers so treated have the properties of wet crosslinked cellulose even though the reaction takes place in the absence of significant amounts of water.

The present invention will be described in greater particularity in combination with the dry crosslinking reaction wherein the fibers are not swollen but are collapsed. The invention will be disclosed specifically with reference to the use of formaldehyde as the dry crosslinking agent. This, however, is for purposes of illustration and it is to be appreciated that other dry crosslinking agents can be used. Additional dry crosslinking agents, for example, include: condensation products of formaldehyde with organic compounds such as urea, thiourea, guanidine, or melamine, which contain at least two active hydrogen groups, particularly dimethylourea and dimethylol ethyleneurea; dicarboxylic acids; dialdehydes; diepoxides; diisocyanates; divinyl compounds; etc.

The most convenient method of carrying out such a dry crosslinking reaction is naturally on the pulpboard itself at which time it is compact and easy to handle, large chambers are not required for curing the product in a large scale production operation, and large ovens would not be required for drying and controlling the moisture content of the product.

Unfortunately, it has been found that such a process of dry crosslinking pulpboard creates considerable problems in the subsequent shredding or grinding step and an unsatisfactory wood pulp fluff is obtained which was not disintegrated properly during the grinding process and which contains severe fiber breakage in the final product. Another important objection is the very high knot content of the wood pulp fluff and the hard fiber clumps or knots which are present sometimes rise as high as about 50–75% and render the product completely unsuitable for many purposes.

In order to avoid such shortcomings, it has been proposed that the pulpboard be difibered first and that the resulting fibrous product be in a substantially individually or loosely associated state and have a multiplicity of relatively large interconnected networks of voids and interfiber spaces at the time of the subsequent crosslinking reaction. In this way, it was hoped that the formation of hard fiber clumps and knots would be avoided. Unfortunately, the additional costs and economic disadvantages of such a system were too great and the search has continued for a better process and a better product.

It is therefore a purpose and object of the present invention to provide a method of dry crosslinking the pulpboard itself in such a way that the pulpboard can be subsequently ground to yield a wood pulp fluff having a very low hard fiber clump or knot content, along with increased fluid absorption and retention capacities, and improved dry and wet resilience.

It has been discovered that such purpose and object may be accomplished by pretreating the commercial pulp before the pulpboard is formed in such a way as to remove or to at least decrease the hemicellulose content thereof below certain minimums whereby the pulpboard made therefrom can be subsequently dry crosslinked and its properties improved without materially increasing the knot content.

The invention will be described in greater detail by reference to the following specification and accompanying drawings wherein there is described and illustrated preferred embodiments of the present invention for disclosure purposes but not for limitative purposes. With reference to the accompanying drawings, FIG. 1 is an idealized drawing, greatly magnified, of two adjacent cellulose fibers, as they are in conventional pulpboard.

FIG. 3 is an idealized drawing, greatly magnified, of two adjacent cellulose fibers of a pulpboard prepared from cellulose fibers pretreated to remove hemicellulose.

FIG. 4 is an idealized drawing, greatly magnified, of two adjacent cellulose fibers of a pulpboard which has been crosslinked, after being given the pretreatment of the present invention to remove hemicellulose.

Figure 1:
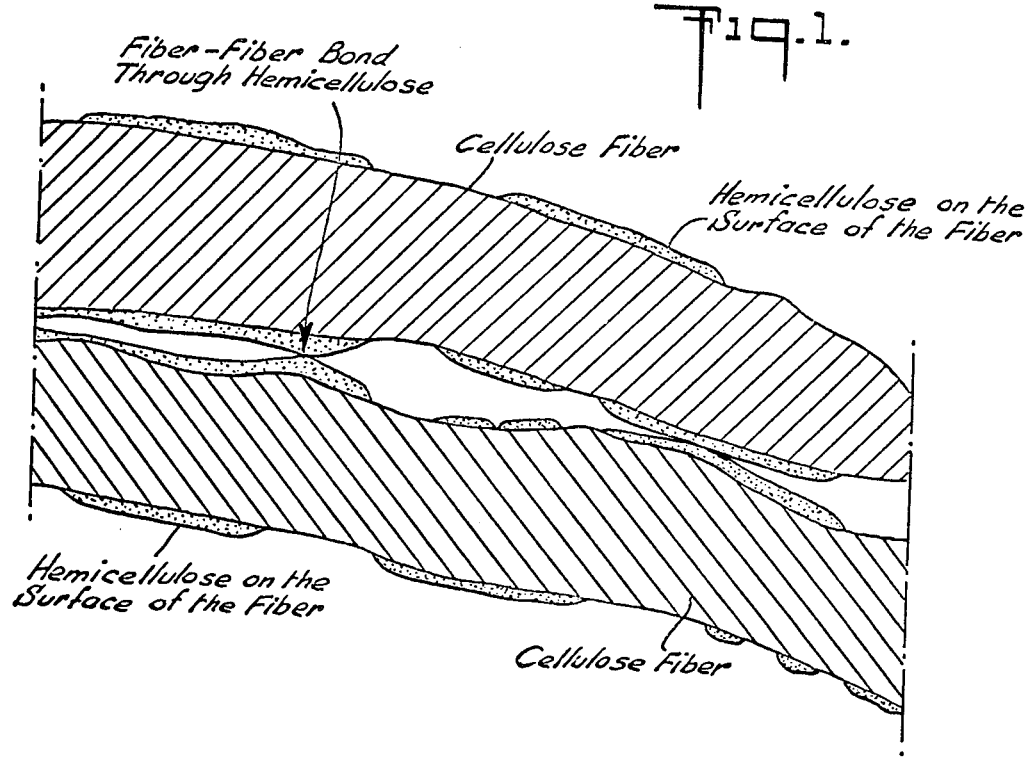

With reference to FIG. 1, there are shown two cellulose fibers having a normal cellulosic structure which, if derived from a softwood, originally had as its major constituents about 40–45% cellulose, 25–30% hemicelluloses, and 25–30% lignin. If derived from a hardwood, the major constituents would change slightly percentagewise to about 45–50% cellulose, 25–35% hemicelluloses, and 20–25% lignin.

During the technical pulping process which is often described as a chemical cooking of wood or a delignification, the majority of the lignin or lignin-like materials are removed, although small amounts thereof still remain and are incorporated into the pulpboard. Also remaining in the pulpboard are varying amounts of hemicelluloses. It is known that considerable amounts of hemicelluloses remain in the fibers after the pulping process, and even after the final bleaching process. As a result, pulpboard having a hemicellulose content of as high as about 15.2% or even higher, is known and will be referred to in greater detail hereinafter.

Hemicelluloses are a group of gummy, amorphous substances intermediate in composition between cellulose and the sugars. They accompany cellulose in the plant cell wall and consist mainly of xylan, mannan, glucomannan, araban, galactan, arabogalactan, uronic acids, plant gums, and related polymers containing residues of L-rhamnose. They are more swellable than cellulose fibers because of their amorphous structure and because of their lower Degree of Polymerization which is believed to be no greater than about 150. A considerable amount of these hemicelluloses are distributed on the surfaces of conventional cellulose fibers, as illustrated in FIG. 1, and may either actually contact each other, or be very close to each other by distances on the order of only a few Angstroms. As a result of this, they help to form good bonding between adjacent fibers during the pulpboard manufacturing process.

Figure 2:
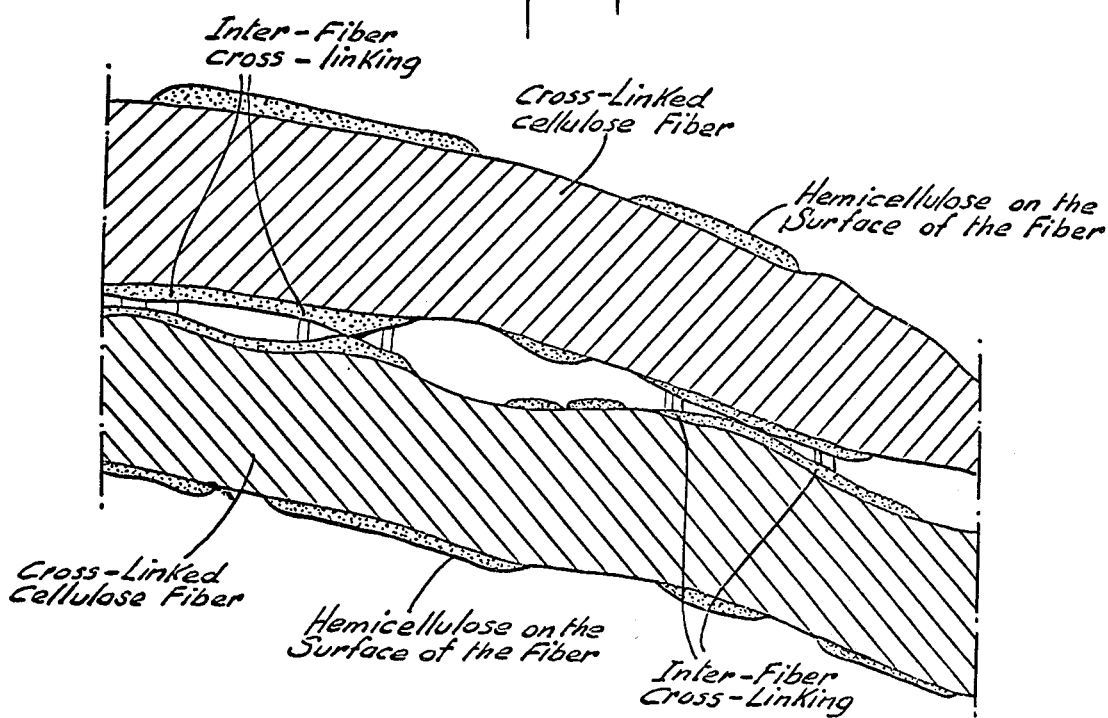
FIG. 2 is an idealized drawing, greatly magnified, of two adjacent cellulose fibers of a conventional pulpboard which has been crosslinked, without the pretreatment of the present invention to remove hemicellulose.

During the crosslinking process which is intended to form crosslinks within the individual cellulose fibers and enhance their absorbent properties, there is also a considerable amount of crosslinking taking place between closely adjacent cellulose fibers, as shown in FIG. 2. This intercrosslinking between fibers easily takes place in the presence of the hemicelluloses preferentially to the amount of intracrosslinking which takes place within the cellulose fiber for many reasons, primarily because of the amorphous structure of the hemicelluloses and their close proximity.

Such intercrosslinking between adjacent cellulose fibers whereby they are chemically and physically adhered is naturally conducive to the formation of knots or clumps of cellulose fibers which prevents proper disintegration of the pulpboard during grinding and leads to highly undesirable high knot contents in the resultant wood pulp fluff.

However, if the hemicellulose is removed during the commercial pulping process, along with the lignin, or if it is removed by a separate alkali treatment after the lignin is removed, or if it is removed at any time prior to the crosslinking reaction, or at least has its content reduced sufficiently, as shown in FIG. 3, then there is very little tendency toward subsequent intercrosslinking between adjacent cellulose fibers, as shown in FIG. 4. The result is a lesser tendency to form knots or clumps of cellulose fibers and a resultant wood pulp fluff with very low knot content.

The hemicelluloses may be removed by any desired pretreatment at any time prior to the crosslinking step. For example, they may be preferentially extracted in substantial amounts or in their entirety by using aqueous solutions of from about 5 to about 12% of a "cold" caustic at temperatures ranging from about 15° to about 35°C. as an additional refining step during the pulping process.

It is not necessary that all of the hemicelluloses be removed completely. Such, of course, will normally yield the best product. However, such complete removal is uneconomical unless the requirements of a specific product are sufficiently demanding as to require it.

Within the more normal commercial requirements such as uses in absorbent products such as sanitary napkins, diapers, hospital underpads, filter pads, surgical dressings, tampons, and the like, a knot content in the wood pulp fluff of below about 12%, after a 60-minute formaldehyde dry crosslinking, as described herein, is deemed acceptable. A knot content of about 15% would be considered marginal but still acceptable for the above-mentioned products.

Figure 6:
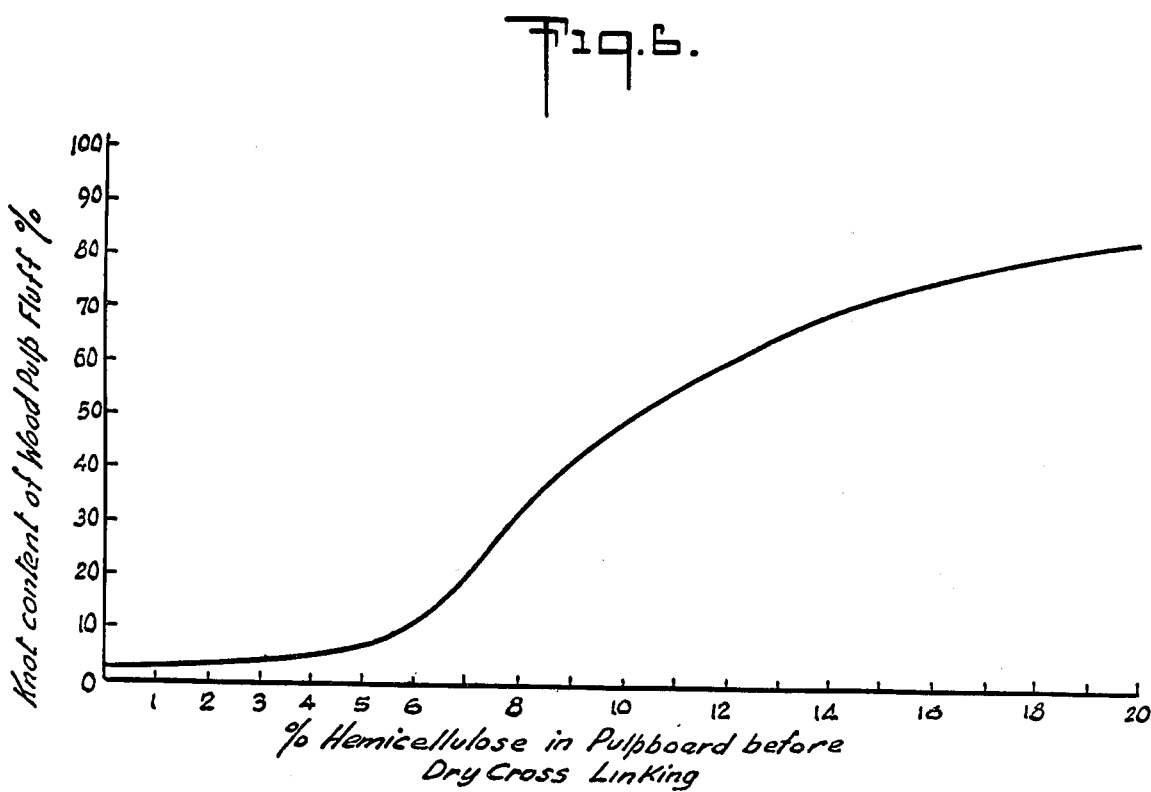
FIG. 6 is a graph showing the relationship between the percent of hemicellulose in the pulpboard before crosslinking and the knot content (percent) in the wood pulp fluff after grinding.
Figure 7:
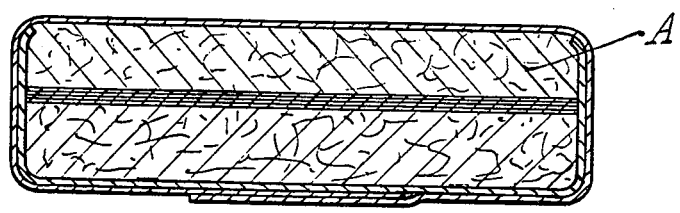
FIG. 7 is a cross-sectional view of a sanitary napkin incorporating the dry crosslinked, low hemicellulose content, low knot content fibrous absorbent materials A of the present invention.
Figure 8:
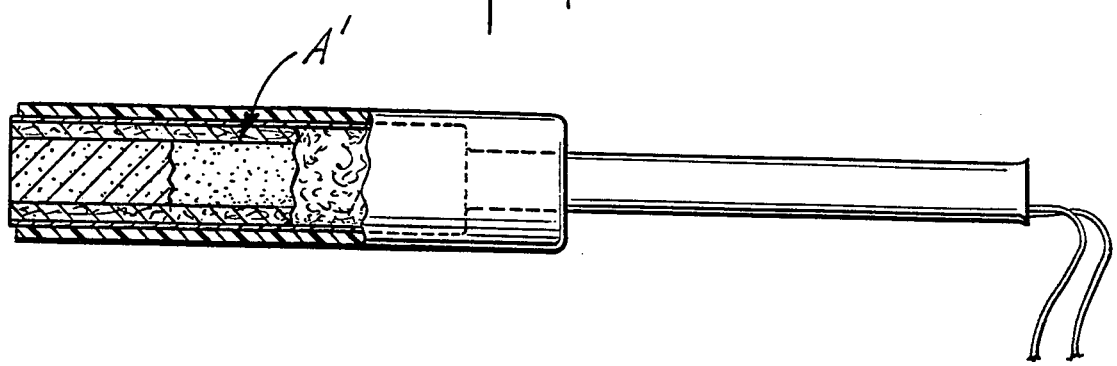
FIG. 8 is a plan view, partially cut away, of a catamenial tampon incorporating the dry crosslinked, low hemicellulose content, low knot content fibrous absorbent materials A' of the present invention.
Figure 9:
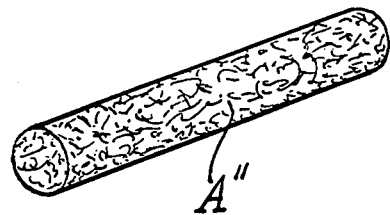
FIG. 9 is a perspective view of a dental roll incorporating the dry crosslinked, low hemicellulose content, low knot content fibrous absorbent materials A'' of the present invention.

Reference to FIG. 6 reveals that under normal circumstances, if one were to start with a pulpboard having a hemicellulose content of about 7% or under, and dry crosslink that pulpboard by means of formaldehyde for about 60 minutes, as described herein, then the knot content of the wood pulp fluff derived from grinding that pulpboard, as described herein, is in the average range of about 15% or less and is suitable for the purposes of the present invention. As used herein, therefore, the term "low hemicellulose content" will include pulpboard containing about 7% hemicellulose or less. Reference to FIG. 6 will also indicate that a pulpboard having a hemicellulose content of about 6% will normally yield, after dry crosslinking and grinding, a wood pulp fluff having an average knot content of about 12%.

The invention will be described in greater particularity by reference to the following examples which are used for illustrative purposes and are not to be construed as limitative of the broader aspects of the present invention, except as set forth in the appended claims.

Although these examples are carried out with a southern pine kraft pulp, it is to be appreciated that such is merely for illustrative purposes and that the principles of the present invention are equally applicable to pulps derived from any of the presently known processes, or combinations thereof. Examples of pulps derived from known processes are: sulfite pulps in which the cooking liquor, calcium bisulfite, is acid, or sodium sulfite which is neutral or slightly alkaline; soda pulps in which the cooking liquor, caustic soda, is alkaline; sulfate pulps in which the cooking liquor, sodium hydroxide and sodium sulfide, is alkaline; etc. Semichemical, mechanical, and groundwood pulps are also of use.

EXAMPLE I

Three samples of pulpboard (southern pine, kraft pulp) which are differentially treated with caustic during the pulping process to remove different amounts of hemicelluloses are prepared to the following specifications (Table I):

TABLE I

| Hemicellulose content | 1 Low | 2 Medium | 3 High |
|---|---|---|---|
| Pulpboard density (g./cc.) | 0.58 | 0.58 | 0.58 |
| Fiber Classification: | | | |
| Screen size 20 | 69.1 | 73.9 | 57.8 |
| Screen size 35 | 15.3 | 12.9 | 29.0 |
| Screen size 65 | 8.8 | 5.4 | 5.8 |
| Screen size 150 | 2.8 | 1.6 | 1.6 |
| Fines | 4.3 | 8.5 | 15.2 |
| α-cellulose | 95.7 | 91.5 | 84.8 |

TABLE I-continued

| Hemicellulose content | 1 Low | 2 Medium | 3 High |
|---|---|---|---|
| Pulpboard density (g./cc.) | 0.58 | 0.58 | 0.58 |
| Fiber Classification: | | | |
| Hemicelluloses | 4.3 | 8.5 | 15.2 |

These samples are crosslinked by being immersed in a solution containing by volume 10% Formalin (37% formaldehyde), 9% hydrochloric acid (36% HCl), and 81% glacial acetic acid. Separate samples are maintained in the crosslinking solution at room temperature for 5 minutes, 15 minutes, and 60 minutes, then immersed in a series of solutions of 5% sodium bicarbonate until neutralization is complete, then rinsed in running water, and finally air dried at room temperature. Control samples are used for comparison purposes and are merely washed in rrunning water without any crosslinking treatment and then are air dried. The formaldehyde add-on is noted in Table 2.

TABLE 2

| | 1 | 2 | 3 |
|---|---|---|---|
| Hemicellulose Content | Low | Medium | High |
| Formaldehyde add-on | | | |
| (Percent) (5 minutes) | 0.283 | 0.280 | 0.314 |
| (15 minutes) | 0.517 | 0.474 | — |
| (60 minutes) | 1.306 | 1.124 | 0.858 |

The grinding of the various samples of pulpboard is carried out in a Weber hammer mill and the knot content of the resulting wood pulp fluff samples is determined according to the constant air-blowing technique. This involves placing a 5 gram sample in the bottom of a 1000 ml. burette and admitting air through the petcock at the bottom at a controlled constant flow rate of 3.5 cubic feet per minute to get a tumbling action of the sample, thereby causing the individualized fibers of the sample to escape through the open top end of the burette but leaving the heavier knots or clumps at the bottom. The knots are then removed and weighed and the knot content (percent) determined (Table 3).

TABLE 3

| Sample | percent of Sample Remaining 1 | 2 | 3 |
|---|---|---|---|
| Hemicellulose content | Low | Medium | High |
| No crosslinking | 2 | 2 | 51 |
| 5 minutes crosslinking | 2 | 4 | 76 |
| 15 minutes crosslinking | 3 | 9 | 76 |
| 60 minutes crosslinking | 3 | 37 | 75 |

Figure 5:
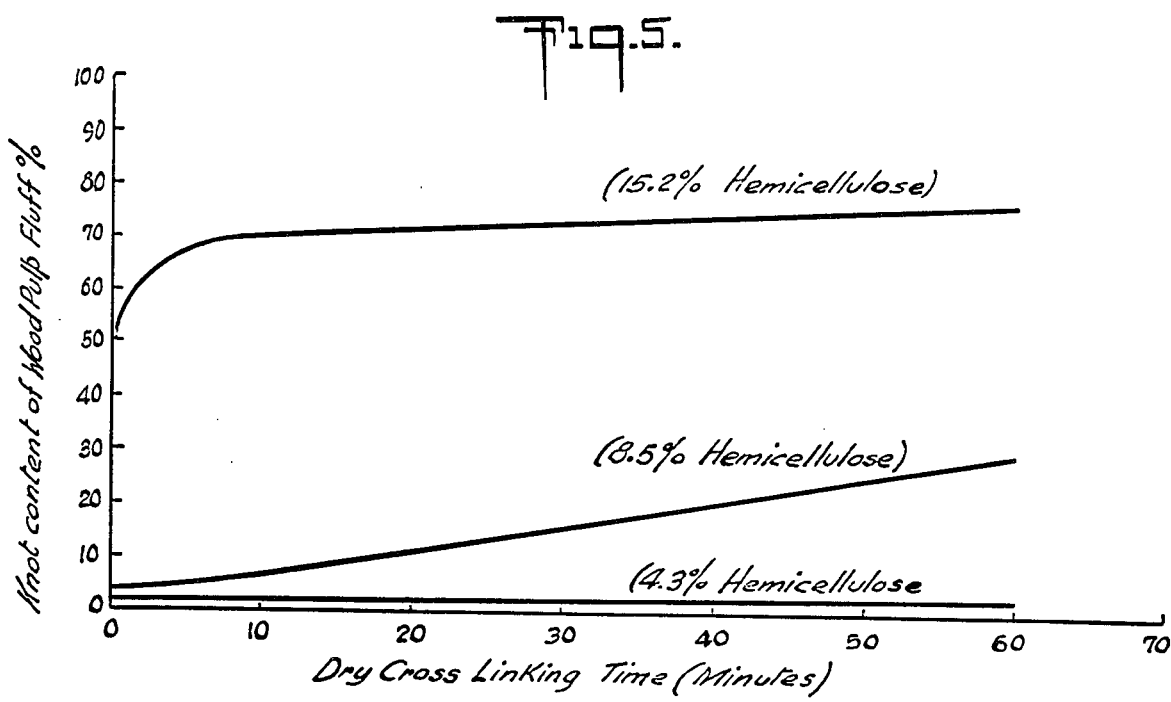
FIG. 5 is a graph showing the relationship between the increase in dry crosslinking time to the change in knot content of wood pulp fluff derived from three sources and having three different percentages of hemicellulose content.

These results are set forth in FIG. 5 of the drawings. It is quite apparent that crosslinking had no material effect on the knot content of sample 1 (4.3% hemicelluloses). This sample had a knot content of 3% after 60 minutes of formaldehyde crosslinking and is suitable for use as an absorbent in a sanitary napkin. However, crosslinking has serious effects on samples 2 and 3 (8.5% hemicellulose and 15.2% hemicellulose, respectively) and neither sample is suitable for use as an absorbent in a sanitary napkin. The knot content of wood pulp fluff derived from these latter samples are noted as 37% and 75%, after a 60-minute formaldehyde crosslinking treatment. These values are noted in FIG. 6.

EXAMPLE II

The procedures of Example I are followed substantially as set forth therein except that a ground Natchez pulp (southern pine, kraft pulp) is used. The hemicellulose content of the pulpboard is about 9%. A control sample which is not crosslinked is used and develops a knot content of 14% in the groundwood pulp fluff which would be marginally acceptable for many absorbent products. After dry crosslinking another sample (also 9% hemicellulose) by formaldehyde for 60 minutes as described previously, and grinding in a Weber mill, the knot content of the groundwood pulp fluff is determined to be 45% which renders it unsatisfactory for most absorbent purposes.

EXAMPLE III

Additional 0.5 gram samples of pulpboard No. 1 (4.3% hemicellulose) and pulpboard No. 2 (8.5% hemicellulose) prepared as set forth in Example I and conditioned at 72°F. and 65% relative humidity are used to determine wet bluk volume and absorbent capacity (water).

TABLE 4

| Sample No. 1 | Density gms./cc. | Wet Bulk Volume cc./gm. | Absorbent Capacity cc./gm. |
|---|---|---|---|
| (Control) | 0.034 | 16.24 | 14.72 |
| (Crosslinked, 60 mins.) | 0.035 | 19.18 | 17.85 |

It is to be noted (Table 4) that in this sample containing low hemicellulose content of only 4.3%, the density did not change materially and that the wet bulk volume increased 18% and the absorbent capacity increased 21% which is excellent.

TABLE 5

| Sample No. 2 | Density gms./cc. | Wet Bulk Volume cc./gm. | Absorbent Capacity cc./gm. |
|---|---|---|---|
| (Control) | 0.035 | 16.35 | 15.24 |
| (Crosslinked, 60 mins.) | 0.049 | 17.15 | 15.74 |

It is to be noted (Table 5) that in this sample containing higher hemicellulose content of 8.5%, the density increased markedly and the wet bulk volume increased only 4.9% and the absorbent capacity increased only 3.3% which is not significant. The deleterious effects of the hemicellulose on the properties of wet bulk volume and absorbent capacity is clearly demonstrated.

EXAMPLE IV

For determining the dry and wet resilience of the low hemicellulose fibers, similar samples are prepared as in Example III. For determining the dry resilience, samples are conditioned at 72°F. and 65% relative humidity. For determining the wet resilience, samples are placed in petridishes containing sufficient water to saturate the samples which are permitted to remain there for several minutes before testing begins.

The dry control sample (hemicellulose content =4.3), upon application of 200 grams/cm.$^2$ pressure, compressed to 12% of its original bulk volume, and recovered to 31% of its original bulk volume upon removal of the pressure. The dry resilience is therefore 31%.

The wet control sample (also hemicellulose content=4.3) collapsed to 55% of its original bulk volume upon being wetted, then compressed to 10% of its original bulk volume upon application of 200 grams/cm.$^2$, and recovered to 23% of its original bulk volume upon removal of the pressure. The wet resilience is 41%.

The dry crosslinked sample (hemicellulose content =4.3), upon application of 200 grams/cm.$^2$ pressure, compressed to 42% of its original bulk volume, and recovered to 59% of its original bulk volume upon removal of pressure. The dry resilience is 59% which is a very great improvement over the dry resilience of 31% of the uncrosslinked control sample.

The wet crosslinked sample (also hemicellulose content = 4.3) collapsed to 67% of its original bulk volume upon being wetted, then compressed to 14% of its original bulk volume upon application of 200 grams/cm.$^2$, and recovered to 31% of its original bulk volume upon removal of the pressure. The wet resilience is 47% which is an improvement over the wet resilience of 41% of the control uncrosslinked sample.

The improvement in dry and wet resilience due to crosslinking is evident from the results of this example.

EXAMPLE V

Additional samples of pulpboard 1 and pulpboard 2, as described in Example I, are ground in a commercial Fitzpatrick hammer mill rather than a Weber hammer mill to determine the effect, if any, of the use of a different grinding mill.

Pulpboard sample 1, having a low hemicellulose content of about 4.3 percent is ground in a commerical Fitzpatrick hammer mill without any prior treatment of any kind. The knot content is determined to be about 12%. A control pulpboard sample, treated with a running water wash and air drying (no crosslinking) is similarly ground and the knot content is determined to be about 10 percent. When exposed to a 60-minute dry crosslinking by formaldehyde, and then ground similarly, the knot content is determined to be only 8 percent. This ground product is acceptable for the purposes of the present invention.

Pulboard sample 2, having a higher hemicellulose content of about 8.5 percent is similarly tested and the knot contents are determined to be 21 percent, 19 percent, and 57 percent, respectively. This ground product is unacceptable for the purposes of the present invention.

The desirability of a lower hemicellulose content in the pulpboard is thus illustrated again.

Although the present invention has been described with particular reference in the preceding examples and in the specification to cellulose fibers derived from wood, it is to be appreciated that the principles are equally applicable to other cellulosic fibrous materials which also contain sufficient hemicelluloses as to interfere with a subsequent crosslinking process. Examples of such other fibrous materials include esparto grass, straw, and the like, as well as industrial waste products such as cotton seed hulls, corn cobs, corn stalks, peanut shells, etc.

It is not necessary that the de-hemicellulosed, crosslinked cellulose fibers be used as the sole constituent of the absorbent portion of the product involved. It may be blended, if desired, in proportions as low as 10% by weight up to 90% with other fibers or other fibrous materials, depending upon the requirements of the particular product. Such other fibers and other fibrous materials include cotton fibers, cotton linters, rayon, wood pulp, cotton batting, synthetic fibers, such as cellulose esters notably cellulose acetate, polyesters from dihydric alcohols and terephthalic acid such as "Dacron" and "Kodel", acrylics containing at least 85% by weight of acrylonitrile such as "Acrilan" and "Orlon", modacrylics containing less than 85% but at least 35% of acrylonitrile such as "Dynel" and "Verel", polyamides such as nylon 6 and nylon 6/6, polyolefins such as polyethylene and polypropylene, spandex fibers derived from polyurethane such as "Lycra" and "Vyrene", fluorocarbons such as "Teflon" TFE and FEP, etc.

The blending of such materials need not be uniform and the de-hemicellulosed, crosslinked cellulosic may be used as the top or an intermediate layer in a laminated structure; as the centrally located, internal, concentric core or the hollow cylindrical externally positioned, wrapping sheath in a composite tampon construction; or the like.

Other changes, variations, and modifications apparent to a person skilled in the art may be resorted to, without departing from the scope of the present invention which is defined in the following claims.

What is claimed is:

1. A method of making pulpboard for grinding into pulp fluff of improved dry and wet resilience and increased fluid absorption and retention capacity from cellulose fibers having a high hemicellulose content comprising:
    treating said cellulose fibers to reduce said hemicellulose content to no more than about 7%;
    forming a pulpboard from said treated cellulosic fibers; and
    dry crosslinking said fibers in said pulpboard form to result in a pulpboard having a knot content of less than 15%.

2. The method of claim 1 wherein said cellulosic fibers are treated by extracting said hemicellulose with an aqueous solution of from about 5 percent to about 12 percent caustic at a temperature of from about 15° to about 35°C.

3. The method of claim 1 wherein said dry crosslinking is accomplished by introducing said pulpboard to an aqueous bath comprising crosslinking agent and catalyst, driving off the water in a heating step and reacting said crosslinking agent with said cellulose in a curing step.

* * * * *